US008399407B2

(12) United States Patent
Weiss

(10) Patent No.: US 8,399,407 B2
(45) Date of Patent: Mar. 19, 2013

(54) NON-STANDARD INSULIN ANALOGUES

(75) Inventor: Michael A. Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 12/884,943

(22) Filed: Sep. 17, 2010

(65) Prior Publication Data

US 2011/0077196 A1  Mar. 31, 2011

Related U.S. Application Data

(60) Provisional application No. 61/243,249, filed on Sep. 17, 2009.

(51) Int. Cl.
*A61K 38/28* (2006.01)
*A61P 3/10* (2006.01)
*C07K 14/62* (2006.01)

(52) U.S. Cl. .......................... 514/5.9; 514/6.9
(58) Field of Classification Search .......................... None
See application file for complete search history.

(56) References Cited

U.S. PATENT DOCUMENTS

| 5,149,716 | A | 9/1992 | Vertesy et al. |
| 5,149,777 | A | 9/1992 | Hansen et al. |
| 5,491,216 | A | 2/1996 | Hoffmann et al. |
| 5,506,202 | A | 4/1996 | Vertesy et al. |
| 5,618,913 | A | 4/1997 | Brange et al. |
| 5,698,669 | A | 12/1997 | Hoffmann et al. |
| 5,700,662 | A | 12/1997 | Chance et al. |
| 5,716,927 | A | 2/1998 | Balschmidt et al. |
| 5,977,297 | A | 11/1999 | Obermeier et al. |
| 6,011,007 | A | 1/2000 | Havelund et al. |
| 6,221,633 | B1 | 4/2001 | Ertl et al. |
| 6,268,335 | B1 | 7/2001 | Brader |
| 6,465,426 | B2 | 10/2002 | Brader |
| 6,531,448 | B1 | 3/2003 | Brader |
| 6,630,348 | B1 | 10/2003 | Lee et al. |
| 7,129,211 | B2 | 10/2006 | Bhattacharya et al. |
| 7,316,999 | B2 | 1/2008 | Hoeg-Jensen et al. |
| 7,547,821 | B2 | 6/2009 | Moloney et al. |
| 2001/0036916 | A1 | 11/2001 | Brader |
| 2002/0082199 | A1 | 6/2002 | Brader |
| 2003/0104981 | A1 | 6/2003 | Mandic |
| 2003/0144181 | A1 | 7/2003 | Brader |
| 2004/0014660 | A1 | 1/2004 | During et al. |
| 2004/0053816 | A1 | 3/2004 | Bhattacharya et al. |
| 2004/0214988 | A1 | 10/2004 | Tirrell et al. |
| 2005/0014679 | A1 | 1/2005 | Beals et al. |
| 2005/0039235 | A1 | 2/2005 | Moloney et al. |
| 2005/0176621 | A1 | 8/2005 | Brader et al. |
| 2006/0217290 | A1 | 9/2006 | Kohn et al. |
| 2007/0129284 | A1 | 6/2007 | Kjeldsen et al. |
| 2008/0146492 | A1 | 6/2008 | Zimmerman et al. |
| 2009/0304814 | A1 | 12/2009 | Weiss |
| 2010/0099601 | A1 | 4/2010 | Weiss |
| 2011/0059887 | A1 | 3/2011 | Weiss |
| 2011/0077197 | A1 | 3/2011 | Habermann et al. |
| 2011/0166064 | A1 | 7/2011 | Weiss |
| 2011/0195896 | A1 | 8/2011 | Weiss et al. |

FOREIGN PATENT DOCUMENTS

| EP | 1 090 640 A2 | 4/2001 |
| WO | 2003/053339 A2 | 7/2003 |
| WO | 2005/054291 A1 | 6/2005 |
| WO | 2007/081824 A2 | 7/2007 |
| WO | 2007/096332 A1 | 8/2007 |
| WO | 2007/081824 A3 | 2/2008 |
| WO | 2008/043033 A2 | 4/2008 |
| WO | 2008/043033 A3 | 11/2008 |
| WO | 2009/087081 A2 | 7/2009 |
| WO | 2009/129250 A2 | 10/2009 |
| WO | 2009/132129 A2 | 10/2009 |
| WO | 2010/132129 A3 | 1/2010 |
| WO | 2009/129250 A3 | 2/2010 |
| WO | 2010/014946 A2 | 2/2010 |
| WO | 2010/014946 A3 | 5/2010 |
| WO | 2011/028813 A2 | 3/2011 |
| WO | 2011/072288 A2 | 6/2011 |
| WO | 2011/103575 A1 | 8/2011 |

OTHER PUBLICATIONS

EP 07 84 3856 Supplementary European Search Report, 4 pages; Dec. 11, 2009.
Currie et al.; The influence of glucose-lowering therapies on cancer risk in type 2 diabetes; Diabetologia; 52(9); pp. 1766-1777; Sep. 2009.
Hemkens et al.; Risk of malignancies in patients with diabetes treated with human insulin or insulin analogues: a cohort study; Diabetologia 52(9); pp. 1732-1744; Sep. 2009.
Tuffs; German agency suspects that insulin analogue glargine increases risk of cancer; PubMed; BMJ; 339:b2774; 1 page (no abstract available); Jul. 8, 2009.
Shukla et al.; Analysis of signaling pathways related to cell proliferation stimulated by insulin analogs in human mammary epithelial cell lines; Endrocine-Related Cancer; 16(2); pp. 429-441; Jun. 2009.
Rajpal et al.; Single-Chain Insulins as Receptor Agonists; The Endrocrine Society; 27 pages; Feb. 19, 2009.
Weinstein, et al.; Insulin analogues display IGF-I-like mitogenic and anti-apoptotic activities in cultured cancer cells; Diabetes/Metabolism Research and Reviews; 25(1); pp. 41-49; Jan. 2009.
Zelobowska et al.; Mitogenic potency of insulin glargine; Polish Journal of Endocrinology; vol. 60, No. 1; pp. 34-39; 2009.
Hua et al.; Design of an Active Ultrastable Single-chain Insulin Analog; The Journal of Biological Chemistry; vol. 283, No. 21; pp. 14703-14716; May 23, 2008.

(Continued)

*Primary Examiner* — Gyan Chandra
(74) *Attorney, Agent, or Firm* — Hahn Loeser & Parks LLP; John J. Cunniff

(57) ABSTRACT

An insulin analogue comprises a B-chain polypeptide containing at least one alteration selected from a methylated phenylalanine substitution at position B24 and an addition of two amino acids to the carboxyl end of the B-chain polypeptide. A first amino acid at position B31 is selected from glutamate and aspartate, and a second amino acid at position B32 is selected from glutamate, alanine and aspartate. The methylated phenylalanine may be ortho-monofluoro-phenylalanine, meta-monobromo-phenylalanine or para-monochloro-phenylalanine. The analogue may be an analogue of a mammalian insulin, such as human insulin. A nucleic acid encoding such an insulin analogue is also provided. A method of treating a patient comprises administering a physiologically effective amount of the insulin analogue or a physiologically acceptable salt thereof to a patient.

15 Claims, 9 Drawing Sheets

OTHER PUBLICATIONS

Liefvendahl et al.; Mitogenic effect of the insulin analogue glargine in malignant cells in comparison with insulin and IGF-I; PubMed; 1 page (abstract only); Apr. 7, 2008.

Du et al.; Insulin analogs with B24 or B25 phenylalanine replaced by biphenylalanine; Acta Biochem Biophys Sin; vol. 40, No. 2; pp. 133-139; Feb. 2008.

Mayer et al.; Proliferative effects of insulin analogues on mammary epithelial cells; Archives of Physiology and Biochemistry; 114(1); pp. 38-44; Feb. 2008.

Kohn et al.; pI-shifted insulin analogs with extended in vivo time action and favorable receptor selectivity; PubMed; 28 (4); 1 page (abstract only); Jan. 25, 2007.

Nakagawa, et al.; Chiral Mutagenesis of Insulin; The Journal of Biological Chemistry; vol. 281, No. 31; pp. 22386-22396; Aug. 4, 2006.

Hua et al.; Mechanism of insulin fibrillation—The structure of insulin under amyloidogenic conditions resembles a protein-folding intermediate, Journal of Biological Chemistry; vol. 279, No. 20; pp. 21449-21460, XP002557730, ISSN 0021-9258; May 14, 2004.

Chen et al.; Sequences of B-Chain/Domain 1-10/1-9 of Insulin and Insulin-like Growth Factor 1 Determine Their Different Folding Behavior; Biochemistry; pp. 9225-9233; 2004.

Zakova et al.; Shortened Insulin Analyogues: Marked Changes in Biological Activity Resulting from Replacement of TyrB26 and N-Methylation of Piptide Bonds in the C-Terminus of the B-Chain; Biochemistry; vol. 43; pp. 2323-2331; 2004.

Weiss et al.; Non-standard Insulin Design: Structure-Activity Relationships at the Periphery of the Insulin Receptor; The Journal of Molecular Biology; vol. 315; pp. 103-111; 2002.

Garriques et al.; The effect of mutations on the structure of insulin fibrils studied by Fourier transform infrared (FTIR) spectroscopy and electron microscopy; PubMed; vol. 12; 1 page (abstract only); 2002.

Weiss, et al.; Activities of Monomeric Insulin Analogs at Position A8 Are Uncorrelated with Their Thermodynamic Stabilities; The Journal of Biological Chemistry; vol. 276, No. 43; pp. 40018-40024; Oct. 26, 2001.

Nielsen et al.; Probing the Mechanism of Insulin Fibril Formation with Insulin Mutants; American Chemical Society; Biochemistry; vol. 40; pp. 8397-8409; Jun. 19, 2001.

Olsen et al.; The Relationship Between Insulin Bioactivity and Structure in the NH2-terminal A-chain Helix; Journal of Molecular Biology; vol. 284, Issue 2; pp. 477-488; Nov. 27, 1998.

Kristensen et al.; Alanine Scanning Mutagenesis of Insulin; The Journal of Biological Chemistry; vol. 272, No. 20; pp. 12978-12983; May 16, 1997.

Milazzo et al.; ASPB10 insulin induction of increased mitogenic responses and phenotypic changes in human breast epithelial cells; evidence for enhanced interactions with the insulin-like growth factor-I receptor; PubMed; 18(1); 1 page (abstract only); Jan. 1997.

Doig et al.; N- and C-capping preferences for all 20 amino acids in {alpha}-helical peptides; Protein Science; vol. 4; pp. 1325-1335; 1995.

Kaarsholm et al.; Engineering Stability of the Insulin Monomer Fold with Application to Structure-Activity Relationships; Biochemistry; 32 (40); pp. 10773-10778; Oct. 1993.

Mirmira et al.; Role of the Phenylalanine B24 Side Chain in Directing Insulin Interaction with Its Receptor; The Journal of Biological Chemistry; vol. 264, No. 11; pp. 6349-6354; Apr. 15, 1989.

Zhao et al.; Design of an insulin analog with enhanced receptor binding selectivity: rationale, structure, and therapeutic implications; J. Biol. Chem. 284(46); Sep. 22, 2009; pp. 32178-32187.

Sreekanth et al.; Structural interpretation of reduced insulin activity as seen in the crystal structure of human Arg-insulin; Biochimie; 90(3); Sep. 22, 2007; pp. 467-473.

Kohn et al.; pI-shifted insulin analogs with extended in vivo time action and favorable receptor selectivity; Peptides; 28 (4); Jan. 25, 2007; pp. 935-948.

Sleiker et al.; Modifications in the B10 and B26-30 regions of the B chain of human insulin alter affinity for the human IGF-I receptor more than for the insulin receptor; Diabetologia; 40 Suppl. 2; Jul. 1997; pp. S54-S61.

Summ et al.; Binding of insulin analogs to partially purified insulin receptor from rat liver membrane (author's trans.); Hoppe Seylers Z. Physiol. Chem.; 357(5); May 1976; pp. 683-693 (Abstract only—1 page).

PCT/US2010/047546 International Search Report and Written Opinion dated May 23, 2011.

PCT/US2010/060085 International Search Report and Written Opinion dated Sep. 16, 2011.

PCT/US11/25730 International Search Report and Written Opinion dated Jul. 22, 2011.

EP 09 80 3678 Supplementary European Search Report dated Jan. 30, 2012.

Blanquart et al.; Characterization of IRA/IR hybrid insulin receptors using bioluminescence resonance energy transfer; Biochemical Pharmacology 76 (2008); Jul. 27, 2008, pp. 873-883.

Duckworth et al.; Degradation products of insulin generated by hepatocytes and by insulin protease; Journal of Biological Chemistry, vol. 263, No. 4, Apr. 6, 1988; pp. 1826-1833.

Haijuan Du et al.; Insulin analogs with B24 or B25 phenylalanine replaced by bipheylalanine; ACTA Biochimica et Biophysica Sinica, vol. 40, No. 2, 2006, pp. 133-139.

Huang et al,; Structure-Specific Effects of Protein on Cross β Assembly: Studies of Insulin Fibrillation; Biochemistry 2006, 45, Aug. 4, 2006, pp. 10278-10293.

Liu et al.; Utilization of combined chemical modification to enhance the blood-brain barrier permeability and pharmacological activity of endomorphin-a, JPET 106, 106484, Jun. 27, 2006, pp. 1-43.

Mirmira et al.; Disposition of the phenylalanine B25 side chain during insulin-receptor and insulin-insulin interactions, Biochemistry; vol. 30, No. 33; May 1, 1991; pp. 8222-8229.

Mirmira et al.; Importance of the character and configuration of residues B24 B25 and B26 in insulin-receptor interactions, Journal of Biological Chemistry, vol. 266, No. 3; Jan. 25, 1991; pp. 1428-1436.

Stemaszynska et al.; N-(2-Oxoacyl)amino Acids and Nitriles as Final Products of Dipeptide Chlorination Mediated by the Myeloperoxidase/H202/Cl-System, European Journal of Biochemistry, vol. 92, No. 1, Sep. 25, 1978, pp. 301-308.

Wan et al,; Enhancing the Activity of Insulin at the Receptor Interface: Crystal Structure and Photo-Cross-Linking of A8 Analogues; Biochemistry 2004, 43; Nov. 25, 2004; pp. 16119-16133.

Yang et al.; An Achilles' heel in an amyloidogenic protein and its repair: insulin fibrillation and therapeutic design; J Biol Chem. Apr. 2010 2:285(14):10806-21.

PROINSULIN

MODEL

SEQUENCE LISTING

```
<160> NUMBER OF SEQ ID NOS: 26

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20
```

```
<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa = CH3-Phe
<220> FEATURE:
<221> NAME/KEY: MISC_FEATURE
<222> LOCATION: (28)..(28)
<223> OTHER INFORMATION: Xaa = Asp, Pro, Lys or Arg
<220> FEATURE:
<221> NAME/KEY: MISC_FEATURE
<222> LOCATION: (29)..(29)
<223> OTHER INFORMATION: Xaa = Lys or Pro

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr
            20                  25                  30

<210> SEQ ID NO 5
<211> LENGTH: 32
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa = Asp, Pro, Lys or Arg
<220> FEATURE:
<221> NAME/KEY: MISC_FEATURE
<222> LOCATION: (29)..(29)
<223> OTHER INFORMATION: Xaa = Lys or Pro
<220> FEATURE:
<221> NAME/KEY: MISC_FEATURE
<222> LOCATION: (31)..(31)
<223> OTHER INFORMATION: Xaa = Glu or Asp
<220> FEATURE:
<221> NAME/KEY: MISC_FEATURE
<222> LOCATION: (32)..(32)
<223> OTHER INFORMATION: Xaa = Glu, Ala or Asp

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Xaa Thr Xaa Xaa
            20                  25                  30

<210> SEQ ID NO 6
<211> LENGTH: 32
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa = Asp, Pro, Lys or Arg
<220> FEATURE:
```

```
<221> NAME/KEY: MISC_FEATURE
<222> LOCATION: (29)..(29)
<223> OTHER INFORMATION: Xaa = Lys or Pro

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Xaa Thr Glu Glu
            20                  25                  30

<210> SEQ ID NO 7
<211> LENGTH: 32
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa = Asp, Pro, Lys or Arg
<220> FEATURE:
<221> NAME/KEY: MISC_FEATURE
<222> LOCATION: (29)..(29)
<223> OTHER INFORMATION: Xaa = Lys or Pro

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Xaa Thr Glu Ala
            20                  25                  30

<210> SEQ ID NO 8
<211> LENGTH: 32
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa = Asp, Pro, Lys or Arg
<220> FEATURE:
<221> NAME/KEY: MISC_FEATURE
<222> LOCATION: (29)..(29)
<223> OTHER INFORMATION: Xaa = Lys or Pro

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Xaa Thr Ala Glu
            20                  25                  30

<210> SEQ ID NO 9
<211> LENGTH: 32
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: Xaa = Asp, Pro, Lys or Arg
<220> FEATURE:
<221> NAME/KEY: MISC_FEATURE
<222> LOCATION: (29)..(29)
<223> OTHER INFORMATION: Xaa = Lys or Pro

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Xaa Thr Asp Asp
            20                  25                  30

<210> SEQ ID NO 10
```

<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa = CH3-Phe

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Lys Pro Thr
            20                  25                  30

<210> SEQ ID NO 11
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa = CH3-Phe

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Asp Lys Thr
            20                  25                  30

<210> SEQ ID NO 12
<211> LENGTH: 32
<212> TYPE: PRT
<213> ORGANISM: Homo sapiens

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr Glu Glu
            20                  25                  30

<210> SEQ ID NO 13
<211> LENGTH: 32
<212> TYPE: PRT
<213> ORGANISM: Homo sapiens

<400> SEQUENCE: 13

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr Glu Glu
            20                  25                  30

<210> SEQ ID NO 14
<211> LENGTH: 32
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa = CH3-Phe
<220> FEATURE:
<221> NAME/KEY: MISC_FEATURE
<222> LOCATION: (28)..(28)
<223> OTHER INFORMATION: Xaa = Asp, Pro, Lys or Arg
<220> FEATURE:
<221> NAME/KEY: MISC_FEATURE
<222> LOCATION: (29)..(29)
<223> OTHER INFORMATION: Xaa = Lys or Pro
<220> FEATURE:

```
<221> NAME/KEY: MISC_FEATURE
<222> LOCATION: (31)..(31)
<223> OTHER INFORMATION: Xaa = Glu or Asp
<220> FEATURE:
<221> NAME/KEY: MISC_FEATURE
<222> LOCATION: (32)..(32)
<223> OTHER INFORMATION: Xaa = Glu, Ala or Asp

<400> SEQUENCE: 14

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Xaa
            20                  25                  30

<210> SEQ ID NO 15
<211> LENGTH: 32
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa = CH3-Phe
<220> FEATURE:
<221> NAME/KEY: MISC_FEATURE
<222> LOCATION: (31)..(31)
<223> OTHER INFORMATION: Xaa = Glu or Asp
<220> FEATURE:
<221> NAME/KEY: MISC_FEATURE
<222> LOCATION: (32)..(32)
<223> OTHER INFORMATION: Xaa = Glu, Ala or Asp

<400> SEQUENCE: 15

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Lys Pro Thr Xaa Xaa
            20                  25                  30

<210> SEQ ID NO 16
<211> LENGTH: 31
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa = CH3-Phe

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Pro Thr Glu Glu
            20                  25                  30

<210> SEQ ID NO 17
<211> LENGTH: 32
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa = CH3-Phe

<400> SEQUENCE: 17

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Asp Pro Thr Glu Glu
            20                  25                  30

<210> SEQ ID NO 18
```

```
<211> LENGTH: 52
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = His or Phe
<220> FEATURE:
<221> NAME/KEY: MISC_FEATURE
<222> LOCATION: (24)..(24)
<223> OTHER INFORMATION: Xaa = CH3-Phe
<220> FEATURE:
<221> NAME/KEY: MISC_FEATURE
<222> LOCATION: (26)..(26)
<223> OTHER INFORMATION: Xaa = Tyr or Phe
<220> FEATURE:
<221> NAME/KEY: MISC_FEATURE
<222> LOCATION: (28)..(28)
<223> OTHER INFORMATION: Xaa = Pro, Lys or Asp
<220> FEATURE:
<221> NAME/KEY: MISC_FEATURE
<222> LOCATION: (29)..(29)
<223> OTHER INFORMATION: Xaa = Lys or Pro
<220> FEATURE:
<221> NAME/KEY: MISC_FEATURE
<222> LOCATION: (31)..(31)
<223> OTHER INFORMATION: Xaa = 0-35 of any amino acid or a break in the
      amino acid chain
<220> FEATURE:
<221> NAME/KEY: MISC_FEATURE
<222> LOCATION: (35)..(35)
<223> OTHER INFORMATION: Xaa = His or Glu
<220> FEATURE:
<221> NAME/KEY: MISC_FEATURE
<222> LOCATION: (39)..(39)
<223> OTHER INFORMATION: Xaa = His or Thr

<400> SEQUENCE: 18

Xaa Val Asn Gln His Leu Cys Gly Ser His Leu Val Glu Ala Leu Tyr
1               5                   10                  15

Leu Val Cys Gly Glu Arg Gly Xaa Phe Xaa Thr Xaa Xaa Thr Xaa Gly
            20                  25                  30

Ile Val Xaa Gln Cys Cys Xaa Ser Ile Cys Ser Leu Tyr Gln Leu Glu
        35                  40                  45

Asn Tyr Cys Asn
    50

<210> SEQ ID NO 19
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = CH3-Phe

<400> SEQUENCE: 19

Gly Xaa Phe Tyr Thr Lys Pro Thr
1               5

<210> SEQ ID NO 20
<211> LENGTH: 8
<212> TYPE: PRT
<213> ORGANISM: Homo sapiens

<400> SEQUENCE: 20

Gly Phe Phe Tyr Thr Pro Lys Thr
1               5

<210> SEQ ID NO 21
<211> LENGTH: 8
```

```
<212> TYPE: PRT
<213> ORGANISM: Homo sapiens

<400> SEQUENCE: 21

Asp Tyr Lys Asp Asp Asp Lys
1               5

<210> SEQ ID NO 22
<211> LENGTH: 89
<212> TYPE: DNA
<213> ORGANISM: Homo sapiens

<400> SEQUENCE: 22
tttgtgaacc aacacctgtg cggctcacac ctggtggaag ctctctacct agtgtggggg    60
aacgaggcta gttctacaca cccaagacc                                     89

<210> SEQ ID NO 23
<211> LENGTH: 90
<212> TYPE: DNA
<213> ORGANISM: Homo sapiens

<400> SEQUENCE: 23
tttgttaacc aacatttgtg tggttctcat ttggttgaag ctttgtactt ggtttgtggt    60
gaaagaggtt agttttacac tccaaagact                                    90

<210> SEQ ID NO 24
<211> LENGTH: 261
<212> TYPE: DNA
<213> ORGANISM: Homo sapiens

<400> SEQUENCE: 24
tttgtgaacc aacacctgtg cggctcacac ctggtggaag ctctctacct agtgtgcggg    60
gaacgaggct agttctacac acccaagacc cgccggagg cagaggacct gcaggtgggg   120
caggtggagc tgggcggcgg ccctggtgca ggcagcctgc agcccttggc cctggagggg   180
tccctgcaga agcgtggcat tgtgaacaa tgctgtacca gcatctgctc cctctaccag    240
ctggagaact actgcaacta g                                            261

<210> SEQ ID NO 25
<211> LENGTH: 261
<212> TYPE: DNA
<213> ORGANISM: Homo sapiens

<400> SEQUENCE: 25
tttgttaacc aacatttgtg tggttctcat ttggttgaag ctttgtactt ggtttgtggt    60
gaaagaggtt agttttacac tccaaagact agaagagaag ctgaagattt gcaagttggt   120
caagttgaat tgggtggtgg tccaggtgct ggttctttgc aaccattggc tttggaaggt   180
tctttgcaaa agagaggtat tgttgaacaa tgttgtactt ctatttgttc tttgtaccaa   240
ttggaaaact actgtaacta a                                            261

<210> SEQ ID NO 26
<211> LENGTH: 32
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa = CH3-Phe or Phe
<220> FEATURE:
<221> NAME/KEY: MISC_FEATURE
<222> LOCATION: (28)..(28)
```

-continued

```
<223> OTHER INFORMATION: Xaa = Asp, Pro, Lys or Arg
<220> FEATURE:
<221> NAME/KEY: MISC_FEATURE
<222> LOCATION: (29)..(29)
<223> OTHER INFORMATION: Xaa = Lys or Pro
<220> FEATURE:
<221> NAME/KEY: MISC_FEATURE
<222> LOCATION: (31)..(31)
<223> OTHER INFORMATION: Xaa = Glu, Asp or no amino acid
<220> FEATURE:
<221> NAME/KEY: MISC_FEATURE
<222> LOCATION: (32)..(32)
<223> OTHER INFORMATION: When Xaa at Residue 31 is no amino acid, Xaa at
      Residue 32 is no amino acid and vice versa
<220> FEATURE:
<221> NAME/KEY: MISC_FEATURE
<222> LOCATION: (32)..(32)
<223> OTHER INFORMATION: Xaa = Glu, Ala, Asp or no amino acid

<400> SEQUENCE: 26

Phe Val Asn Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Xaa
            20                  25                  30
```

NON-STANDARD INSULIN ANALOGUES

CROSS REFERENCE TO RELATED APPLICATIONS

This application claims benefit of pending U.S. Provisional Application No. 61/243,249 filed on Sep. 17, 2009.

STATEMENT REGARDING FEDERALLY SPONSORED RESEARCH OR DEVELOPMENT

This invention was made with government support under cooperative agreements awarded by the National Institutes of Health under grant numbers DK40949 and DK074176. The U.S. government may have certain rights to the invention.

INCORPORATION BY REFERENCE OF MATERIAL SUBMITTED ELECTRONICALLY

The material contained in the Sequence Listing provide herewith in ASCII compliant format in the text file entitled "200512-89_ST25.txt" created on Sep. 17, 2010 and containing 12,345 bytes, is hereby incorporated by reference herein.

BACKGROUND OF THE INVENTION

This invention relates to a polypeptide hormone analogue that exhibits enhanced activity and augmented resistance to thermal degradation. More particularly, this invention relates to insulin analogues that are modified by the incorporation of a non-standard amino acids and nonstandard sequences.

The engineering of ultra-stable proteins, including therapeutic agents and vaccines, may have broad societal benefits in regions of the developing world where electricity and refrigeration are not consistently available. An example of a therapeutic protein susceptible to thermal degradation is provided by insulin. The challenge posed by its physical degradation is deepened by the pending epidemic of diabetes mellitus in Africa and Asia. Because fibrillation poses the major route of degradation above room temperature, the design of fibrillation-resistant formulations may enhance the safety and efficacy of insulin replacement therapy in such challenged regions.

Aromatic side chains may engage in a variety of hydrophobic and weakly polar interactions, involving not only neighboring aromatic rings but also other sources of positive- or negative electrostatic potential. Examples include main-chain carbonyl- and amide groups in peptide bonds. Hydrophobic packing of aromatic side chains can occur within the core of proteins and at non-polar interfaces between proteins.

Administration of insulin has long been established as a treatment for diabetes mellitus. Insulin is a small globular protein that plays a central role in metabolism in vertebrates. Insulin contains two chains, an A chain, containing 21 residues and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). Although the structure of proinsulin has not been determined, a variety of evidence indicates that it consists of an insulin-like core and disordered connecting peptide (FIG. 1B). Formation of three specific disulfide bridges (A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM).

Amino-acid substitutions in insulin have been investigated for effects on thermodynamic stability and biological activity. No consistent relationship has been observed between stability and activity. Whereas some substitutions that enhance thermodynamic stability also enhance binding to the insulin receptor, other substitutions that enhance stability impede such binding. The effects of substitution of $Thr^{A8}$ by several other amino acids has been investigated in wild-type human insulin and in the context of an engineered insulin monomer containing three unrelated substitutions in the B-chain ($His^{B10} \rightarrow Asp$, $Pro^{B28} \rightarrow Lys$, and $Lys^{B29} \rightarrow Pro$) have been reported. Examples are also known in the art of substitutions that accelerate or delay the time course of absorption. Such substitutions (such as $Asp^{B28}$ in Novalog® and [$Lys^{B28}$, $Pro^{B29}$] in Humalog®) can be and often are associated with more rapid fibrillation and poorer physical stability. Indeed, a series of ten analogues of human insulin have been tested for susceptibility to fibrillation, including $Asp^{B28}$-insulin and $Asp^{B10}$-insulin. All ten were found to be more susceptible to fibrillation at pH 7.4 and 37° C. than is human insulin. The ten substitutions were located at diverse sites in the insulin molecule and are likely to be associated with a wide variation of changes in classical thermodynamic stability. Although a range of effects has been observed, no correlation exists between activity and thermodynamic stability.

Insulin is a small globular protein that is highly amenable to chemical synthesis and semi-synthesis, which facilitates the incorporation of nonstandard side chains. Insulin contains three phenylalanine residues (positions B1, B24, and B25) and a structurally similar tyrosine at position B26. Conserved among vertebrate insulins and insulin-like growth factors, the aromatic ring of $Phe^{B24}$ packs against (but not within) the hydrophobic core to stabilize the super-secondary structure of the B-chain. $Phe^{B24}$ lies at the classical receptor-binding surface and has been proposed to direct a change in conformation on receptor binding.

The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the insulin molecule to increase or decrease the risk of fibrillation is highly unpredictable.

Fibrillation, which is a serious concern in the manufacture, storage and use of insulin and insulin analogues for diabetes treatment, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, diabetic individuals optimally must keep insulin refrigerated prior to use. Fibrillation of insulin or an insulin analogue can be a particular concern for diabetic patients utilizing an external insulin pump, in which small amounts of insulin or insulin analogue are injected into the patient's body at regular intervals. In such a usage, the insulin or insulin analogue is not kept refrigerated within the pump apparatus and fibrillation of insulin can result in blockage of the catheter used to inject insulin or insulin analogue into the body, potentially resulting in unpredictable blood glucose level fluctuations or even dangerous hyperglycemia. At least one recent report has indicated that lispro insulin (an analogue in which residues B28 and B29 are interchanged relative to their positions in wild-type human insulin; trade name Humalog®) may be particularly susceptible to fibrillation and resulting obstruction of insulin pump catheters. Insulin exhibits an increase in degradation rate of 10-fold or more for each 10° C. increment in temperature above 25° C., and guidelines call for storage at temperatures <30° C. and preferably with refrigeration.

Insulin fibrillation is an even greater concern in implantable insulin pumps, where the insulin would be contained within the implant for 1-3 months at high concentration and at physiological temperature (i.e. 37° C.), rather than at ambient temperature as with an external pump. Additionally, the agitation caused by normal movement would also tend to accelerate fibrillation of insulin. In spite of the increased potential for insulin fibrillation, implantable insulin pumps are still the subject of research efforts, due to the potential advantages of such systems. These advantages include intraperitoneal delivery of insulin to the portal circulatory system, which mimics normal physiological delivery of insulin more closely than subcutaneous injection, which provides insulin to the patient via the systemic circulatory system. Intraperitoneal delivery provides more rapid and consistent absorption of insulin compared to subcutaneous injection, which can provide variable absorption and degradation from one injection site to another. Administration of insulin via an implantable pump also potentially provides increased patient convenience. Whereas efforts to prevent fibrillation, such as by addition of a surfactant to the reservoir, have provided some improvement, these improvements have heretofore been considered insufficient to allow reliable usage of an implanted insulin pump in diabetic patients outside of strictly monitored clinical trials.

Insulin may be stored in the reservoir of an implantable pump as a concentrated protein solution (2-4 mM). High concentrations are required to extend the time interval between refills (typically 3-4 months in experimental systems described in clinical trials) and to avoid the need for a large reservoir that would be uncomfortable, unsightly, or unsafe for the patient. Insulin at such high concentrations is particularly susceptible to fibrillation. Insulin analogues that combine higher biological activity and augmented resistance to fibrillation would enable pump designs that exhibit smaller reservoirs and/or longer duration between refills.

The functional specificity of proteins used in medical treatment is an important concern in medicine. Binding of protein hormones and growth factors to cognate cellular receptors mediates biological effects. Cross-binding of such protein hormones and growth factors to other receptors can lead to undesired biological effects of treatment. Insulin and insulin analogues regulate metabolism through binding to the insulin receptor (IR) and can mediate undesirable mitogenic effects through binding to the Type I insulin-like growth factor receptor (IGFR). Therefore, there is a need for insulin analogues with decreased binding affinity for IGFR and/or enhanced affinity of the hormone for IR relative to its affinity for IGFR. There is also a need for insulin analogues with enhanced activity and augmented stability while maintaining at least a portion of the biological activity of the parent analogue.

SUMMARY OF THE INVENTION

It is, therefore, an aspect of the present invention to provide an insulin analogue that provides greater stability. It is another aspect of the invention to provide insulin analogues with improved affinity for insulin receptor relative to insulin like growth factor receptor. In one example, this is achieved by methyl modification of an amino acid, where the analogue then maintains at least a portion of biological activity of the corresponding non-methylated insulin or insulin analogue. In another example, this is achieved by adding two amino acids to the carboxy-terminal end of an insulin B-chain polypeptide. In still another example, an insulin analogue may contain both a methyl modification of an amino acid and an addition of two amino acids such a glutamate to the carboxy-terminal end of the insulin B-chain polypeptide.

In general, the present invention provides an insulin analogue comprising a B-chain polypeptide that is nonstandard. In one example, the B-chain polypeptide incorporates a methylated phenylalanine. In one particular example, the methylated phenylalanine is at position B24. In another embodiment, the nonstandard phenylalanine is ortho-mono-methyl-phenylalanine, meta-mono-methyl-phenylalanine or para-mono-methyl-phenylalanine. In another embodiment, the insulin analogue is a mammalian insulin analogue, such as an analogue of human insulin. In one particular set of embodiments, the B-chain polypeptide comprises an amino acid sequence selected from the group consisting of SEQ. ID. NOS. 4, 10, 11 and 14-17, and polypeptides having three or fewer additional amino acid substitutions thereof.

In another example, the insulin analogue includes an addition of two amino acids to the insulin B-chain at the carboxy-terminal end. In one example, the B-chain polypeptide contains a glutamate extension ($Glu^{B31}$) or aspartate ($Asp^{B31}$) extension and an additional extension selected from glutamate ($Glu^{B32}$), alanine ($Ala^{B32}$) and aspartate ($Asp^{B32}$). In one particular example, the addition to the carboxy-terminal end of the insulin B-chain is $Glu^{B31}$, $Glu^{B32}$. In a further example, the insulin analogue includes both a methylated phenylalanine at position B24 and an addition of two amino acids to the insulin B-chain at the carboxy-terminal end. In one particular set of embodiments, the B-chain polypeptide comprises an amino acid sequence selected from the group consisting of SEQ. ID. NOS. 5-9, 12 and 13, and polypeptides having three or fewer additional amino acid substitutions thereof.

In one example of the present invention, the B-chain polypeptide comprises an amino acid sequence that may be generalized as SEQ. ID. NO. 26.

SEQ. ID. NO. 26
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Xaa$_2$-Xaa$_3$-Thr-Xaa$_4$-Xaa$_5$ where $Xaa_1$ is $CH_3$-Phe or Phe, $Xaa_2$ is Asp, Pro, Lys, or Arg, $Xaa_3$ is Lys or Pro, $Xaa_4$ is Glu, Asp or no amino acid, and $Xaa_5$ is Glu, Ala, Asp or no amino acid, with the proviso that when $Xaa_4$ is no amino acid, $Xaa_5$ is no amino acid and vice versa.

Also provided is a nucleic acid encoding an insulin analogue comprising a B-chain polypeptide that incorporates a methylated phenylalanine at position B24. In one example, the methylated phenylalanine is encoded by a stop codon, such as the nucleic acid sequence TAG. An expression vector may comprise such a nucleic acid and a host cell may contain such an expression vector.

In addition or in the alternative, a nucleic acid encoding an insulin analogue may include an addition at the carboxy-terminal end. The addition may include a glutamate extension or an aspartate extension at position B31 and a glutamate, alanine or aspartate extension at position B32.

The invention also provides a method of treating a patient. The method comprises administering a physiologically effective amount of an insulin analogue or a physiologically acceptable salt thereof to the patient, wherein the insulin analogue or a physiologically acceptable salt thereof contains a B-chain polypeptide incorporating a methylated phenylalanine or an extension at positions B31 and B32 as described above, or both. In one embodiment, the methylated phenylalanine in the insulin analogue administered to a patient is located at position B24. In another embodiment, the methylated phenylalanine is ortho-mono-methyl-phenylalanine, meta-mono-methyl-phenylalanine or para-mono-methyl-phenylalanine. In still another embodiment, the insulin analogue is a mammalian insulin analogue, such as an analogue of human insulin. In addition or in the alternative, the extensions at positions B31 and B32 may be selected from a glutamate extension or an aspartate extension at position B31 and a glutamate, alanine or aspartate extension at position B32. In one particular set of embodiments, the B-chain polypeptide comprises an amino acid sequence selected from the group consisting of SEQ. ID. NOS. 5-18 and polypeptides having three or fewer additional amino-acid substitutions thereof.

DETAILED DESCRIPTION OF THE INVENTION

Figure 1A:
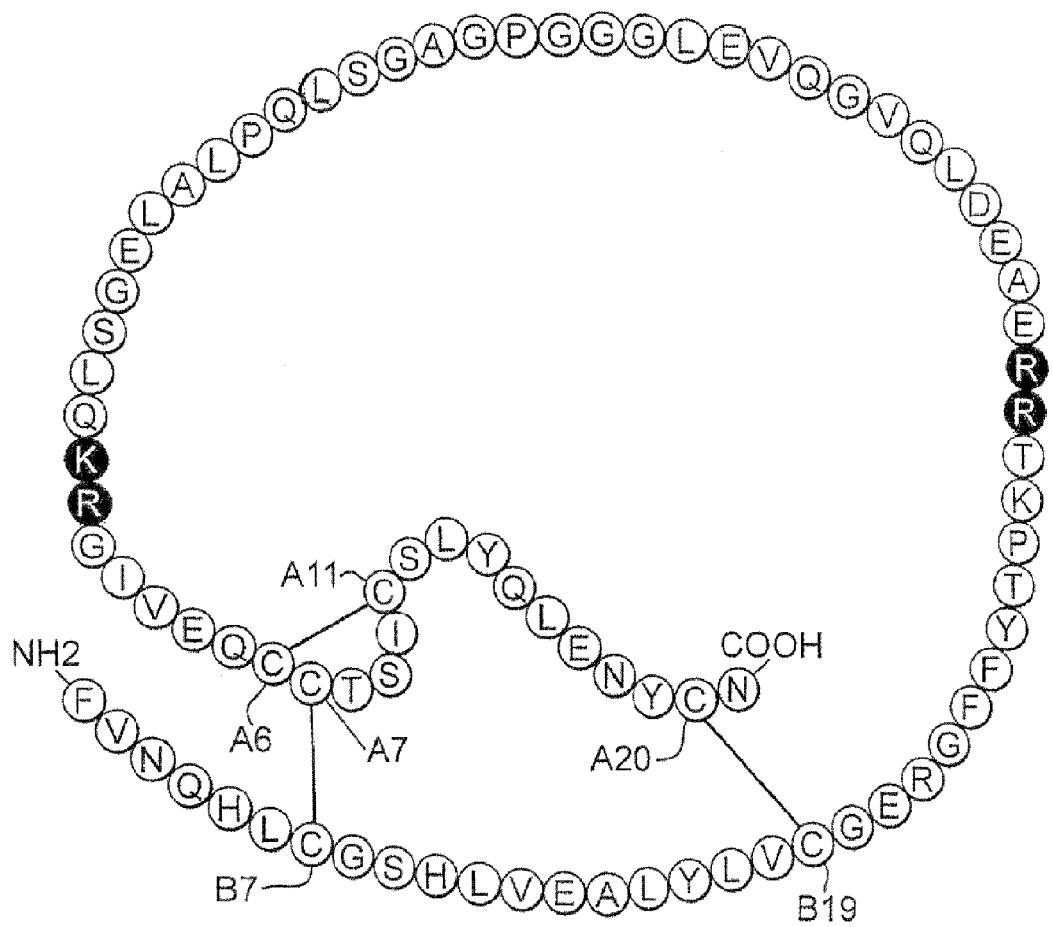
FIG. 1A is a schematic representation of the sequence of human proinsulin including the A- and B-chains and the connecting region shown with flanking dibasic cleavage sites (filled circles) and C-peptide (open circles).
Figure 1B:
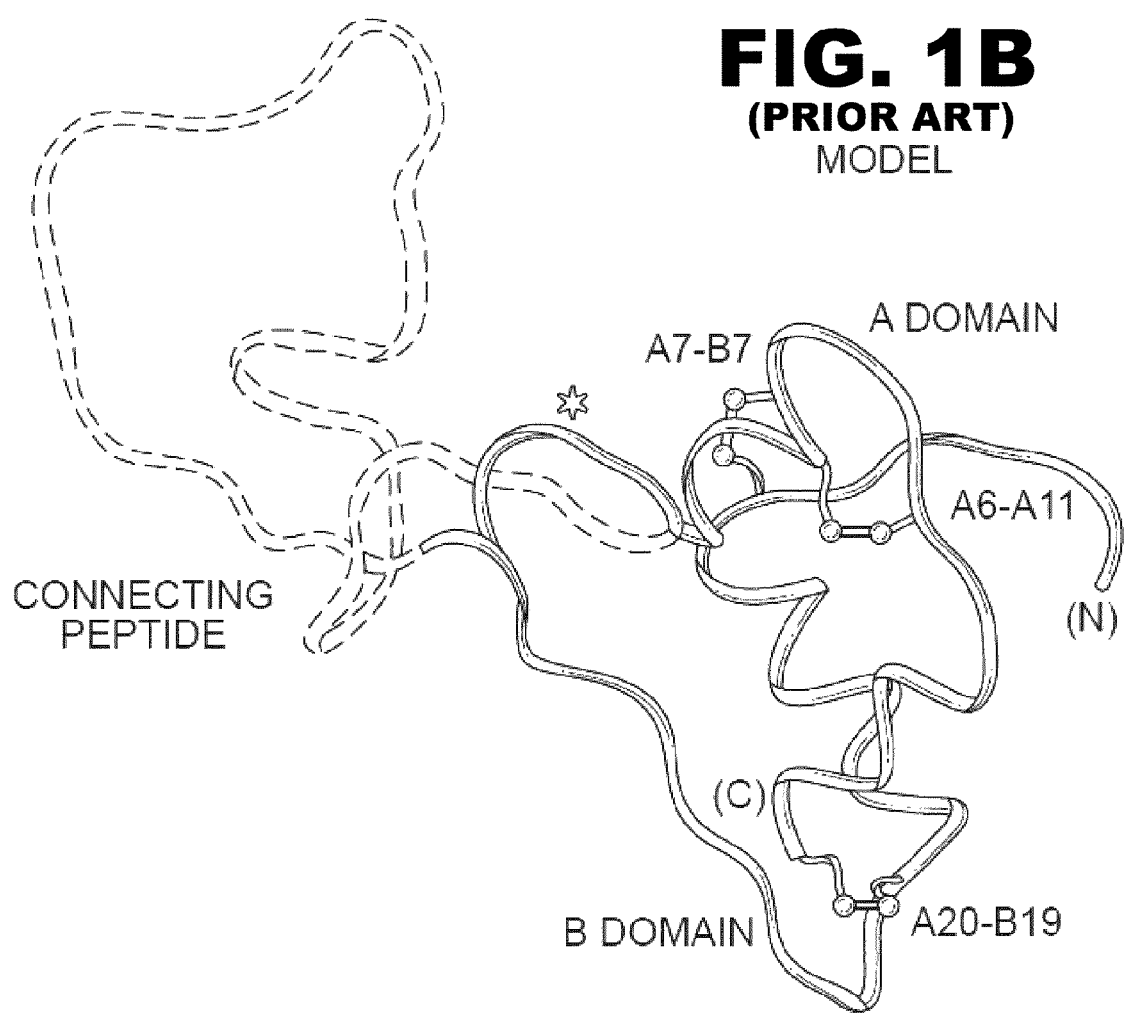
FIG. 1B is a structural model of proinsulin, consisting of an insulin-like moiety and a disordered connecting peptide (dashed line).
Figure 1C:
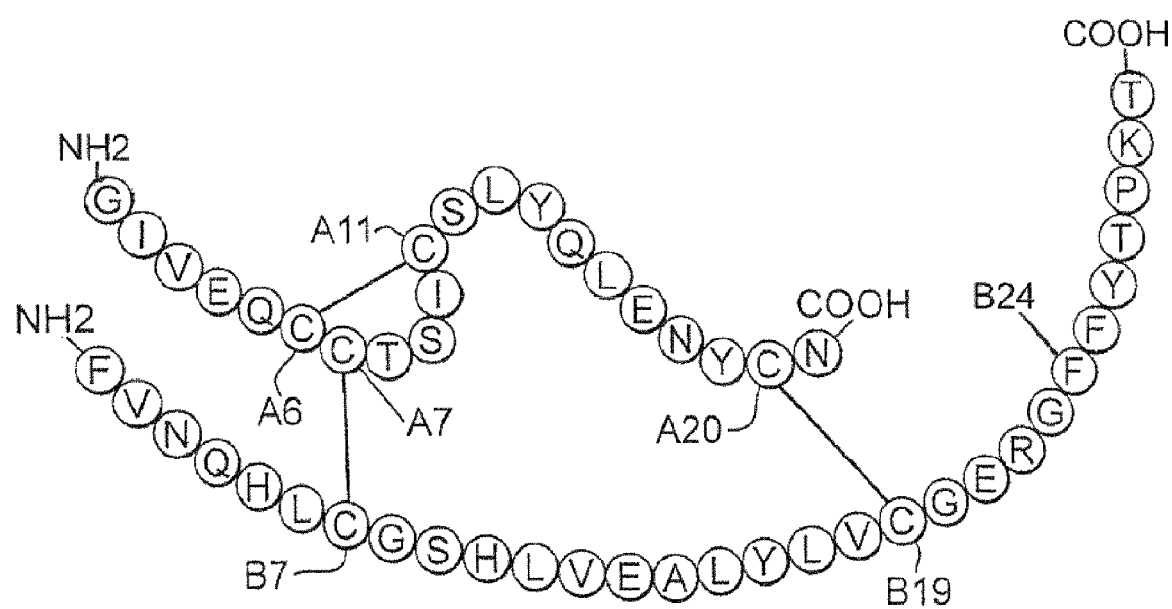
FIG. 1C is a schematic representation of the sequence of human insulin indicating the position of residue B24 in the B-chain.

The present invention is directed an insulin analogue that provides greater activity and stability by substitution of a methylated aromatic amino acid or an extension of the polypeptide sequence, or both, where the analogue then maintains at least a portion of biological activity of the corresponding unmodified insulin or insulin analogue. In one particular embodiment, the present invention provides an insulin analogue that provides greater stability and receptor-binding activity by substitution of phenylalanine at position B24 by a mono-methyl derivative at the ortho (2) position. In other embodiments, related meta and para methyl substituted analogues maintain at least a portion of biological activity of the corresponding unmodified insulin or insulin analogue. One potential application is to augment the physical stability of an insulin analogue while retaining a portion of its biological activity; another application is to calibrate the receptor-binding properties of an insulin analogue to be less than, similar to, or greater than that of human insulin. To these ends, the present invention provides insulin analogues that contain a methylated phenylalanine (Phe) residue as a substitution at position B24.

In addition or in the alternative, an insulin analogue that provides greater activity and stability has a glutamate addition or an aspartate addition at position B31 and a glutamate, alanine or aspartate addition at position B32. In one particular embodiment, the additions at B31 and B32 are both glutamate additions ($Glu^{B31}$, $Glu^{B32}$).

The present invention is not limited, however, to human insulin and its analogues. It is also envisioned that these substitutions may also be made in animal insulins such as porcine, bovine, equine, and canine insulins, by way of non-limiting examples.

Furthermore, in view of the similarity between human and animal insulins, and use in the past of animal insulins in human diabetic patients, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids.

In one example, the insulin analogue of the present invention contains three or fewer conservative substitutions other than the methylated-Phe substitutions and/or B-chain additions of the present invention. In another example, the insulin analogue of the present invention contains one or fewer conservative substitutions other than the methylated-Phe substitutions and/or B-chain additions of the present invention.

As used in this specification and the claims, various amino acids in insulin or an insulin analogue may be noted by the amino acid residue in question, followed by the position of the amino acid, optionally in superscript. The position of the amino acid in question includes the A or B chain of insulin where the substitution is located. Thus, $Phe^{B24}$ denotes a phenylalanine at the twenty fourth amino acid of the B chain of insulin. An addition to an insulin A- or B-chain can similarly be shown with this numbering system by showing the relative position of the addition, regardless of its presence or absence in wild type insulin. For example, although the B-chain polypeptide of wild type human insulin contains 30 amino acids, a glutamate addition on the carboxy-terminal end of the polypeptide may be denoted as $Glu^{B31}$ and a further addition of glutamate on the carboxy-terminal end of the polypeptide may be denoted as $Glu^{B32}$.

Figure 2:
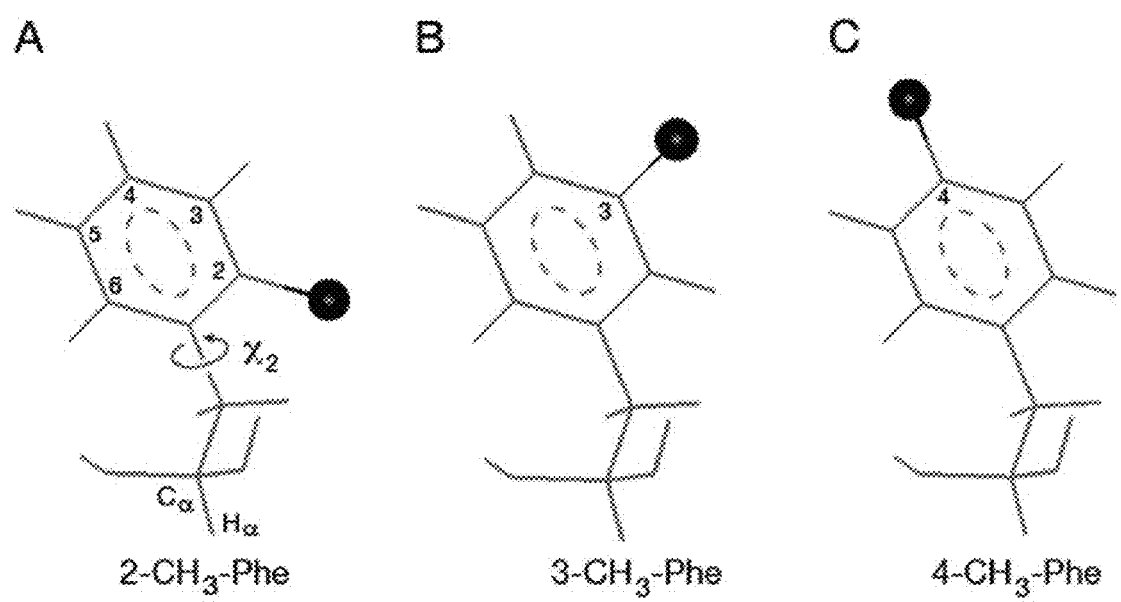
FIG. 2A is a representation of ortho-mono-methyl-phenylalanine (2-$CH_3$-Phe).
FIG. 2B is a representation of meta-mono-methyl-phenylalanine (3-$CH_3$-Phe).
FIG. 2C is a representation of para-mono-methyl-phenylalanine (4-$CH_3$-Phe).

A methylated aromatic amino acid may be indicated with the prefix "$CH_3$-." In the case of phenylalanine, the position of the methyl substituent on the phenyl side chain may be further indicated by the number of the carbon to which the methyl group is attached. Therefore, ortho-mono-methyl-phenylalanine (shown in FIG. 2B) is abbreviated "$2\text{-}CH_3$-Phe," meta-mono-methyl-phenylalanine (shown in FIG. 2C) is abbreviated "$3\text{-}CH_3$-Phe," and para-mono-methyl-phenylalanine (shown in FIG. 2D) is abbreviated "$4\text{-}CH_3$-Phe."

Figure 1D:
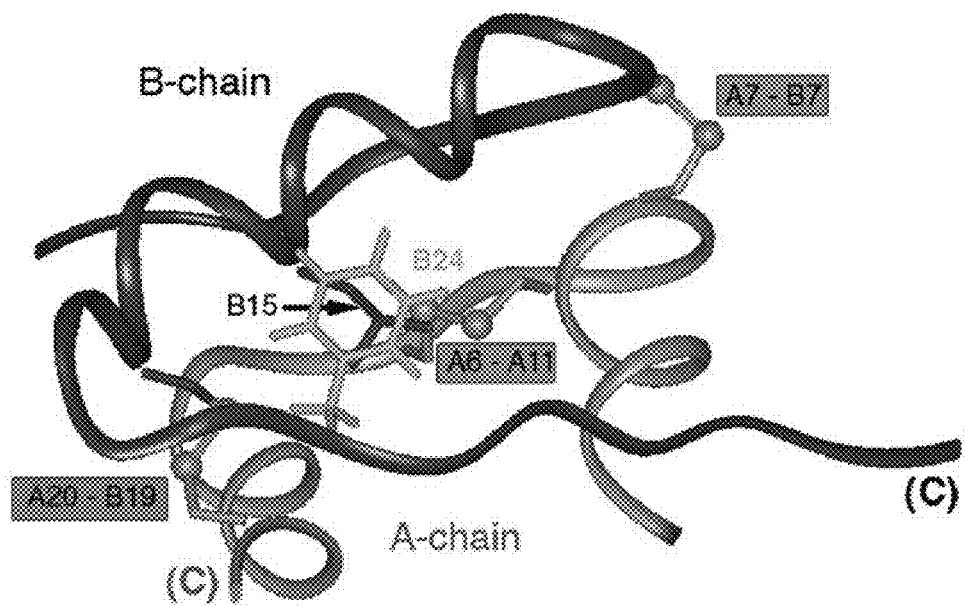
FIG. 1D is a ribbon model of an insulin monomer showing aromatic residue of $Phe^{B24}$ in relation to the three disulfide bridges. The adjoining side chains of $Leu^{B15}$ (arrow) and $Phe^{B24}$ are shown. The A- and B-chain chains are otherwise shown in light and dark gray, respectively, and the sulfur atoms of cysteines as circles.
Figure 1E:
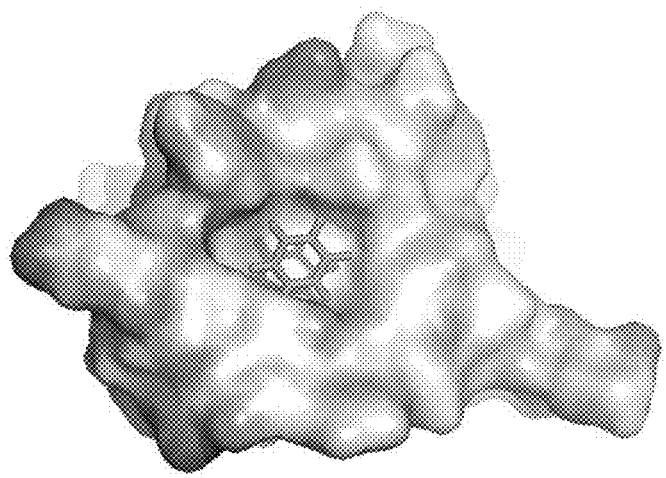
FIG. 1E is a space-filling model of insulin showing the $Phe^{B24}$ side chain within a pocket at the edge of the hydrophobic core.

The phenylalanine at B24 is an invariant amino acid in functional insulin and contains an aromatic side chain. The biological importance of $Phe^{B24}$ in insulin is indicated by a clinical mutation ($Ser^{B24}$) causing human diabetes mellitus. As illustrated in FIGS. 1D and 1E, and while not wishing to be bound by theory, $Phe^{B24}$ is believed to pack at the edge of a hydrophobic core at the classical receptor binding surface. The models are based on a crystallographic protomer (2-Zn molecule 1; Protein Databank identifier 4INS). Lying within the C-terminal β-strand of the B-chain (residues B24-B28), $Phe^{B24}$ adjoins the central a-helix (residues B9-B19). One face and edge of the aromatic ring sit within a shallow pocket defined by $Leu^{B15}$ and $Cys^{B19}$; the other face and edge are exposed to solvent (FIG. 1E). This pocket is in part surrounded by main-chain carbonyl and amide groups and so creates a complex and asymmetric electrostatic environment with irregular steric borders. Irrespective of theory, this structural environment provides an opportunity to optimize hydrophobic packing by extension of the carbon skeleton of the aromatic ring while retaining the weakly polar properties of that ring.

It is envisioned that the substitutions of the present invention may be made in any of a number of existing insulin analogues. For example, the methylated phenylalanine ($CH_3$-Phe) substitutions and/or the B-chain polypeptide extensions provided herein may be made in insulin analogues such as Lispro insulin, insulin Aspart, other modified insulins or insulin analogues, or within various pharmaceutical formulations, such as regular insulin, NPH insulin, lente insulin or ultralente insulin, in addition to human insulin. Aspart insulin contains an $Asp^{B28}$ substitution and is sold as Novalog® whereas Lispro insulin contains $Lys^{B28}$ and $Pro^{B29}$ substitutions and is known as and sold under the name Humalog®. These analogues are described in U.S. Pat. Nos. 5,149,777 and 5,474,978, the disclosures of which are hereby incorporated by reference herein. Both of these analogues are known as fast-acting insulins.

The amino-acid sequence of human proinsulin is provided, for comparative purposes, as SEQ. ID. NO. 1.

```
                                            SEQ. ID. NO. 1
(proinsulin)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn
```

The amino acid sequence of the A chain of human insulin is provided as SEQ. ID. NO. 2.

```
                                            SEQ. ID. NO. 2
(A chain)
Gly-Ile-Val-Glu-Gln-Cys-Cys-Thr-Ser-Ile-Cys-Ser- Leu-Tyr-Gln-Leu-Glu-Asn-Tyr-Cys-Asn
```

The amino acid sequence of the B chain of human insulin is provided as SEQ. ID. NO. 3.

```
                                            SEQ. ID. NO. 3
(B chain)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

The amino acid sequence of a B chain of human insulin may be modified with a substitution of a methylated-Phe at position B24. An example of such a sequence is provided as SEQ. ID. NO 4.

```
                                            SEQ. ID. NO. 4
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa₁-

Phe-Tyr-Thr-Xaa₂-Xaa₃-Thr

[Xaa₁ is CH₃-Phe; Xaa₂ is Asp, Pro, Lys, or Arg;
Xaa₃ is Lys or Pro]
```

A polypeptide sequence of a human insulin B-chain analogue may be modified with an extension of two amino acids on the carboxy-terminal end of the polypeptide. An example of such a sequence is provided as SEQ. ID. NO. 5.

SEQ. ID. NO. 5
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Xaa$_1$-Xaa$_2$-Thr-Xaa$_3$-Xaa$_4$

[Xaa$_1$ is Asp, Pro, Lys, or Arg; Xaa$_2$ is Lys or Pro; Xaa$_3$ is Glu or Asp; Xaa$_4$ is Glu, Ala, or Asp]

In one particular embodiment, the insulin analogue has a B-chain of any of SEQ. ID. NOS. 6-9.

SEQ. ID. NO. 6
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Xaa$_1$-Xaa$_2$-Thr-Glu-Glu

[Xaa$_1$ is Asp, Pro, Lys, or Arg; Xaa$_2$ is Lys or Pro]

SEQ. ID. NO. 7
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Xaa$_1$-Xaa$_2$-Thr-Glu-Ala

[Xaa$_1$ is Asp, Pro, Lys, or Arg; Xaa$_2$ is Lys or Pro]

SEQ. ID. NO. 8
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Xaa$_1$-Xaa$_2$-Thr-Ala-Glu

[Xaa$_1$ is Asp, Pro, Lys, or Arg; Xaa$_2$ is Lys or Pro]

SEQ. ID. NO. 9
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Xaa$_1$-Xaa$_2$-Thr-Asp-Asp

[Xaa$_1$ is Asp, Pro, Lys, or Arg; Xaa$_2$ is Lys or Pro]

Further combinations of other substitutions are also within the scope of the present invention. It is also envisioned that the substitutions and/or additions of the present invention may also be combined with substitutions of prior known insulin analogues. For example, the amino acid sequence of an analogue of the B chain of human insulin containing the Lys$^{B28}$Pro$^{B29}$ (KP) substitutions of lispro insulin (Humalog®), in which one of the methylated Phe substitution may also be introduced, is provided as SEQ. ID. NO. 10. Likewise, the amino acid sequence of an analogue of the B chain of human insulin containing the Asp$^{B28}$ substitution of aspart insulin, in which the F-Phe$^{B24}$ substitution may also be introduced, is provided as SEQ. ID. NO. 11.

SEQ. ID. NO. 10
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Lys-Pro-Thr

[Xaa$_1$ is CH$_3$-Phe]

SEQ. ID. NO. 11
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Asp-Lys-Thr

[Xaa$_1$ is CH$_3$-Phe]

Similarly, the B-chain insulin analogue may contain the KP substitution of Humalog® with a pair of additions to the carboxy-terminal end. Such a polypeptide sequence is provided as SEQ. ID. NO. 12, which has two glutamate additions at the carboxyl end. Alternatively, the B-chain insulin analogue may contain the Asp$^{B28}$ substitution of aspart insulin with a pair of glutamate additions to the carboxy-terminal end, as provided as SEQ. ID. NO. 13.

SEQ. ID. NO. 12
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Lys-Pro-Thr-Glu-Glu

SEQ. ID. NO. 13
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Asp-Lys-Thr-Glu-Glu

Furthermore, a B-chain insulin analogue polypeptide may contain both a methylated phenylalanine at position B24 and an extension of two amino acids at the carboxy-terminal end, as provided by SEQ. ID. NO. 14.

SEQ. ID. NO. 14
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Xaa$_2$-Xaa$_3$-Thr-Xaa$_4$-Xaa$_5$

[Xaa$_1$ is CH$_3$-Phe; Xaa$_2$ is Asp, Pro, Lys, or Arg; Xaa$_3$ is Lys or Pro; Xaa$_4$ is Glu or Asp; Xaa$_5$ is Glu, Ala, or Asp]

In one particular embodiment, a B-chain insulin analogue polypeptide contains a methylated phenylalanine at position B24, an extension of two amino acids at the carboxy-terminal end, and the KP substitution of Humalog® as provided in SEQ. ID. NO. 15. In another particular example, the two added amino acids are both glutamate as provided in SEQ. ID. NO. 16.

SEQ. ID. NO. 15
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Lys-Pro-Thr-Xaa$_2$-Xaa$_3$

[Xaa$_1$ is CH$_3$-Phe; Xaa$_2$ is Glu or Asp; Xaa$_3$ is Glu, Ala, or Asp]

SEQ. ID. NO. 16
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa$_1$-

-continued
Phe-Tyr-Thr-Lys-Pro-Thr-Glu-Glu

[Xaa$_1$ is CH$_3$-Phe]

In still another embodiment, the B-chain insulin analogue polypeptide contains a methylated phenylalanine at position B24, an Asp$^{B28}$ substitution, a Pro$^{B29}$ substitution and a pair of glutamate additions to the carboxy-terminal end (Glu$^{B31}$, Glu$^{B32}$), as provided as SEQ. ID. NO. 17.

SEQ. ID. NO. 17
Phe-Val-Asn-Gln-His-Leu-Cys-Gly-Ser-His-Leu-Val-

Glu-Ala-Leu-Tyr-Leu-Val-Cys-Gly-Glu-Arg-Gly-Xaa$_1$-

Phe-Tyr-Thr-Asp-Pro-Thr-Glu-Glu

[Xaa$_1$ is CH$_3$-Phe]

A mono-methyl-Phe$^{B24}$ substitution may also be introduced in combination with other insulin analogue substitutions such as analogues of human insulin containing H is substitutions at residues A4, A8 and/or B1 as described more fully in co-pending International Application No. PCT/US07/00320 and U.S. application Ser. No. 12/160,187, the disclosures of which are incorporated by reference herein. For example, the CH$_3$-Phe$^{B24}$ substitution may be present with [His$^{A4}$, His$^{A8}$], and/or His$^{B1}$ substitutions in an insulin analogue or proinsulin analogue having the amino acid sequence represented by SEQ. ID. NO. 18, SEQ. ID. NO. 18
Xaa$_1$-Val-Asn-Gln-His-Leu-Cys-Gly-Ser-His-Leu-Val- Glu-Ala-Leu-Tyr-Leu-Val-Cys-Gly-Glu-Arg-Gly-Xaa$_8$-

Phe-Xaa$_2$-Thr-Xaa$_3$-Xaa$_4$-Thr-Xaa$_5$-Gly-Ile-Val-Xaa$_6$-

Gln-Cys-Cys-Xaa$_7$-Ser-Ile-Cys-Ser-Leu-Tyr-Gln-Leu-

Glu-Asn-Tyr-Cys-Asn;

wherein Xaa$_1$ is H is or Phe; wherein Xaa$_2$ is Tyr or Phe, Xaa$_3$ is Pro, Lys, or Asp; wherein Xaa$_4$ is Lys or Pro; wherein Xaa$_6$ is H is or Glu; wherein Xaa$_7$ is H is or Thr; wherein Xaa$_5$ is 0-35 of any amino acid or a break in the amino acid chain; and wherein Xaa$_8$ is CH$_3$-Phe;

and further wherein at least one substitution selected from the group of the following amino acid substitutions is present:
Xaa$_1$ is His; and
Xaa$_7$ is His; and
Xaa$_6$ and Xaa$_7$ together are His.

A mono-methyl-Phe substitution at B24 and/or two amino acid addition may also be introduced into a single chain insulin analogue as disclosed in co-pending U.S. patent application Ser. No. 12/419,169, the disclosure of which is incorporated by reference herein.

Mono-methyl-Phe B24 substitutions were introduced within an engineered insulin monomer of native activity, designated KP-insulin, which contains the substitutions Lys$^{B28}$ (K) and Pro$^{B29}$ (P). These two substitutions on the surface of the B-chain are believed to impede formation of dimers and hexamers. KP-insulin is the active ingredient of Humalog®, currently in clinical use as a rapid-acting insulin analogue formulation. The sequence of the B-chain polypeptide for this variant of KP insulin is provided as SEQ. ID. NO. 6, where Xaa$_1$ is Lys and Xaa$_2$ is Pro.

Analogues of KP-insulin were prepared by trypsin-catalyzed semi-synthesis and purified by high-performance liquid chromatography (Mirmira, R. G., and Tager, H. S., 1989. *J. Biol. Chem.* 264: 6349-6354.) This protocol employs (i) a synthetic octapeptide representing residues (N)-GF*FYT KPT (including modified residue (F*) and "KP" substitutions (underlined); SEQ. ID. NO. 19) and (ii) truncated analogue des-octapeptide[B23-B30]-insulin (SEQ. ID. NO. 15). Because the octapeptide differs from the wild-type B23-B30 sequence (GFFYTPKT; SEQ. ID. NO. 20) by interchange of Pro$^{B28}$ and Lys$^{B29}$ (italics), protection of the lysine ε-amino group is not required during trypsin treatment. In brief, des-octapeptide (15 mg) and octapeptide (15 mg) were dissolved in a mixture of dimethylacetamide/1,4-butandiol/0.2 M Tris acetate (pH 8) containing 10 mM calcium acetate and 1 mM ethylene diamine tetra-acetic acid (EDTA) (35:35:30, v/v, 0.4 mL). The final pH was adjusted to 7.0 with 10 μL of N-methylmorpholine. The solution was cooled to 12° C., and 1.5 mg of TPCK-trypsin was added and incubated for 2 days at 12° C. An additional 1.5 mg of trypsin was added after 24 hr. The reaction was acidified with 0.1% trifluoroacetic acid and purified by preparative reverse-phase HPLC(C4). Mass spectrometry using matrix-assisted laser desorption/ionization time-of-flight (MALDI-TOF; Applied Biosystems, Foster City, Calif.) in each case gave expected values (not shown). The general protocol for solid-phase synthesis is as described (Merrifield et al., 1982. *Biochemistry* 21: 5020-5031). 9-fluoren-9-yl-methoxy-carbonyl (F-moc)-protected phenylalanine analogues were purchased from Chem-Impex International (Wood Dale, Ill.).

Circular dichroism (CD) spectra were obtained at 4° C. and 25° C. using an Aviv spectropolarimeter (Weiss et al., Biochemistry 39: 15429-15440). Samples contained ca. 25 μM DKP-insulin or analogues in 50 mM potassium phosphate (pH 7.4); samples were diluted to 5 μM for guanidine-induced denaturation studies at 25° C. To extract free energies of unfolding, denaturation transitions were fitted by non-linear least squares to a two-state model as described by Sosnick et al., *Methods Enzymol.* 317: 393-409. In brief, CD data$^{\theta(x)}$, where x indicates the concentration of denaturant, were fitted by a nonlinear least-squares program according to $$\theta(x) = \frac{\theta_A + \theta_B e^{-\left(-\Delta G^o_{H_2O} - mx\right)/RT}}{1 + e^{-\left(\Delta G^o_{H_2O} - mx\right)/RT}}$$

where x is the concentration of guanidine and where $\theta_A$ and $\theta_B$ are baseline values in the native and unfolded states. Baselines were approximated by pre- and post-transition lines $\theta_A(x) = \theta_A^{H_2O} + m_A x$ and $\theta_B(x) = \theta_B^{H_2O} + m_B x$. The m values obtained in fitting the variant unfolding transitions are lower than the m value obtained in fitting the wild-type unfolding curve. To test whether this difference and apparent change in $\Delta G_u$ result from an inability to measure the CD signal from the fully unfolded state, simulations were performed in which the data were extrapolated to plateau CD values at higher concentrations of guanidine; essentially identical estimates of $\Delta G_u$ and m were obtained.

Relative activity is defined as the ratio of the hormone-receptor dissociation constants of analogue to wild-type human insulin, as measured by a competitive displacement assay using $^{125}$I-human insulin. An additional insulin receptor-binding assay to monitor changes in activity during the course of incubation of the insulin analogue at 37° C. was performed using a microtiter plate antibody capture as known in the art. Microtiter strip plates (Nunc Maxisorb) were incubated overnight at 4° C. with AU5 IgG (100 μl/well of 40 mg/ml in phosphate-buffered saline). Binding data were analyzed by a two-site sequential model. A corresponding microtiter plate antibody assay using the IGF Type I receptor was employed to assess cross-binding to this homologous receptor. Data were corrected for nonspecific binding (amount of radioactivity remaining membrane associated in the presence of 1 μM human insulin (or in the case of the IGF receptor, 1 μM IGF-1). In all assays the percentage of tracer bound in the absence of competing ligand was less than 15% to avoid ligand-depletion artifacts.

Figure 3:
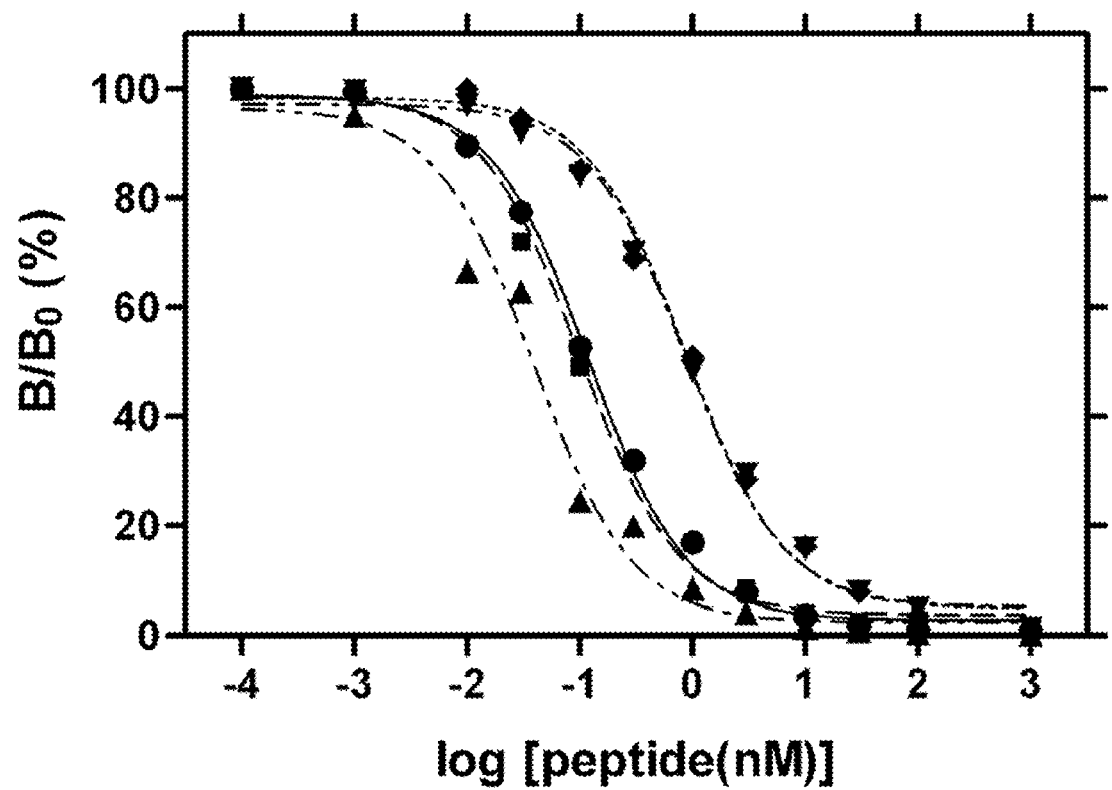
FIG. 3 is a graph showing the results of receptor-binding studies of insulin analogues. Relative activities for the β isoform of the insulin receptor are determined by competitive binding assay in which receptor-bound $^{125}$I-labeled human insulin is displaced by increasing concentrations of human insulin (●) or its analogues: KP-insulin (■), 2-$CH_3$-$Phe^{B24}$-KP-insulin (▲), 3-$CH_3$-$Phe^{B24}$-KP-insulin (▼), 4-$CH_3$-$Phe^{B24}$-KP-insulin (◆).
Figure 4:
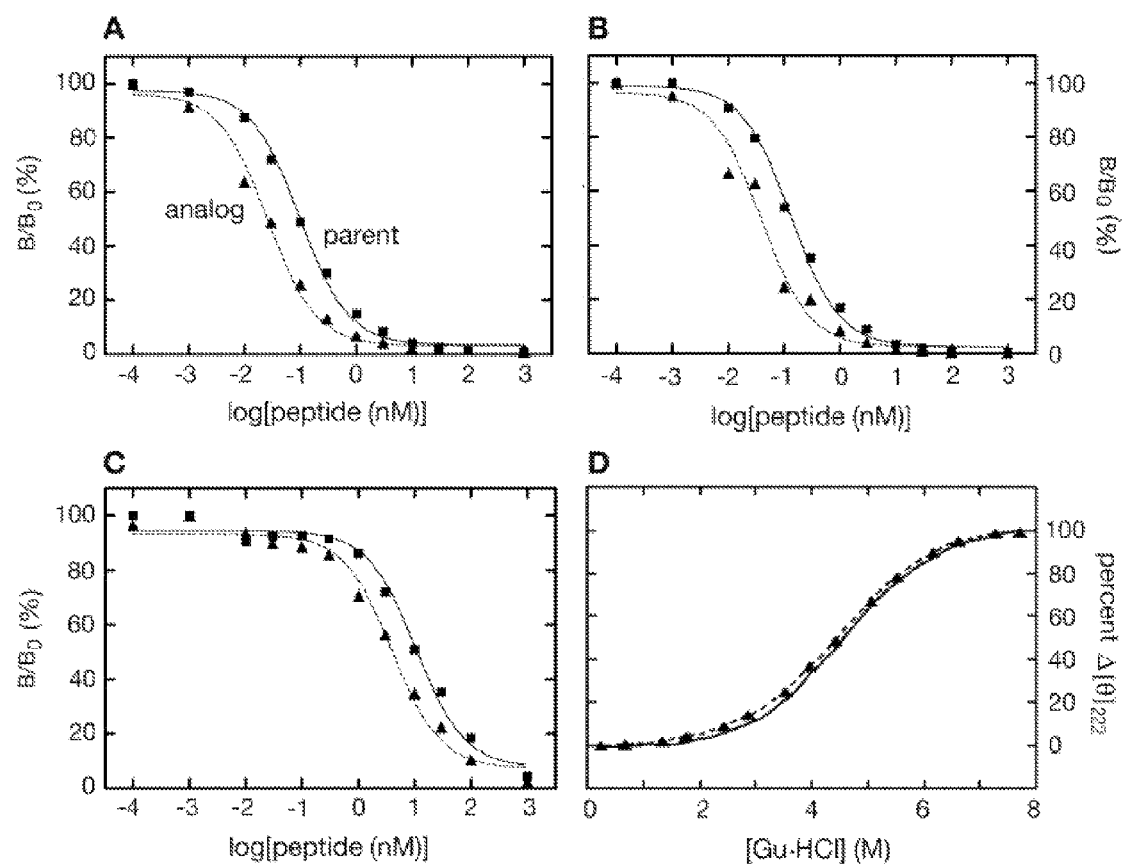
FIG. 4 provides four graphs comparing KP-insulin (■; solid line) and 2-$CH_3$-$Phe^{B24}$-KP-insulin (▲; dashed line) with respect to (A) binding to isoform A of the insulin receptor, (B) binding to isoform B of the insulin receptor, (C) binding to the IGF receptor, and (D) guanidine denaturation studies.

The far-ultraviolet circular dichroism (CD) spectra of the mono-methyl B24 analogues are essentially identical to that of the parent analogue (FIG. 3). The stabilities and receptor-binding activities of the analogues are provided in Table 1. Modified B24 residues were introduced within the context of KP-insulin. Activity values shown are based on ratio of hormone-receptor dissociation constants relative to human insulin; the activity of human insulin is thus 1.0 by definition. Standard errors in the activity values were in general less than 25%. Free energies of unfolding ($\Delta G_u$) at 25° C. were estimated based on a two-state model as extrapolated to zero denaturant concentration. Lag time indicates time (in days) required for initiation of protein fibrillation on gentle agitation at 37° C. in zinc-free phosphate-buffered saline (pH 7.4).

No significant differences were observed in studies of thermodynamic stability ($\Delta\Delta G_u$<0.2 kcal/mole). Nonetheless, the physical stabilities of the 2-methyl-B24 analogue was augmented as evaluated in triplicate during incubation in 60 μM phosphate-buffered saline (PBS) at pH 7.4 at 37° C. under gentle agitation. The samples were observed for 15 days or until signs of precipitation or frosting of the glass vial were observed. Whereas KP-insulin forms fibrils within 3±1 days, the 2-methyl-Phe$^{B24}$ analogue exhibited a lag time of 11-12 days. Substitution of a single methyl group to the aromatic ring of Phe$^{B24}$ is thus able to augment the physical stability of a monomeric insulin analogue.

Dissociation constants ($K_d$) were determined as described by Whittaker and Whittaker (2005. *J. Biol. Chem.* 280: 20932-20936), by a competitive displacement assay using $^{125}$I-Tyr$^{414}$-insulin (kindly provided by Novo-Nordisk) and the purified and solubilized insulin receptor (isoform B or A) in a microtiter plate antibody capture assay with minor modification; transfected receptors were tagged at their C-terminus by a triple repeat of the FLAG epitope (DYKDDDDK; SEQ. ID. NO. 21) and microtiter plates were coated by anti-FLAG M2 monoclonal antibody (Sigma). The percentage of tracer bound in the absence of competing ligand was less than 15% to avoid ligand-depletion artifacts. Binding data were analyzed by non-linear regression using a heterologous competition model (Wang, 1995, *FEBS Lett.* 360: 111-114) to obtain dissociation constants. Results are provided in Table 1 (dissociation constants in units of nanomolar). The ortho-CH$_3$-Phe$^{B24}$ modification enhances binding of KP-insulin to the B isoform of the insulin receptor by ca. threefold and the A isoform by ca. fourfold. A similar increase was observed in cross-binding to the IGF receptor. Corresponding modification at the meta or para positions impaired binding to the B isoform by at least eightfold.

TABLE 1

Binding of Insulin Analogues to the Insulin Receptor

| Sample | IR-B binding | IR-A binding |
|---|---|---|
| KP-insulin | 0.064 ± 0.009 nM | 0.057 ± 0.008 nM |
| 2-CH$_3$-Phe$^{B24}$-KP-insulin | 0.021 ± 0.004 nM | 0.014 ± 0.002 nM |

TABLE 1-continued

Binding of Insulin Analogues to the Insulin Receptor

| Sample | IR-B binding | IR-A binding |
|---|---|---|
| 3-CH$_3$-Phe$^{B24}$-KP-insulin | 0.49 ± 0.07 nM | ND |
| 4-CH$_3$-Phe$^{B24}$-KP-insulin | 0.60 ± 0.08 nM | ND |

ND, not determined.

Figure 5:
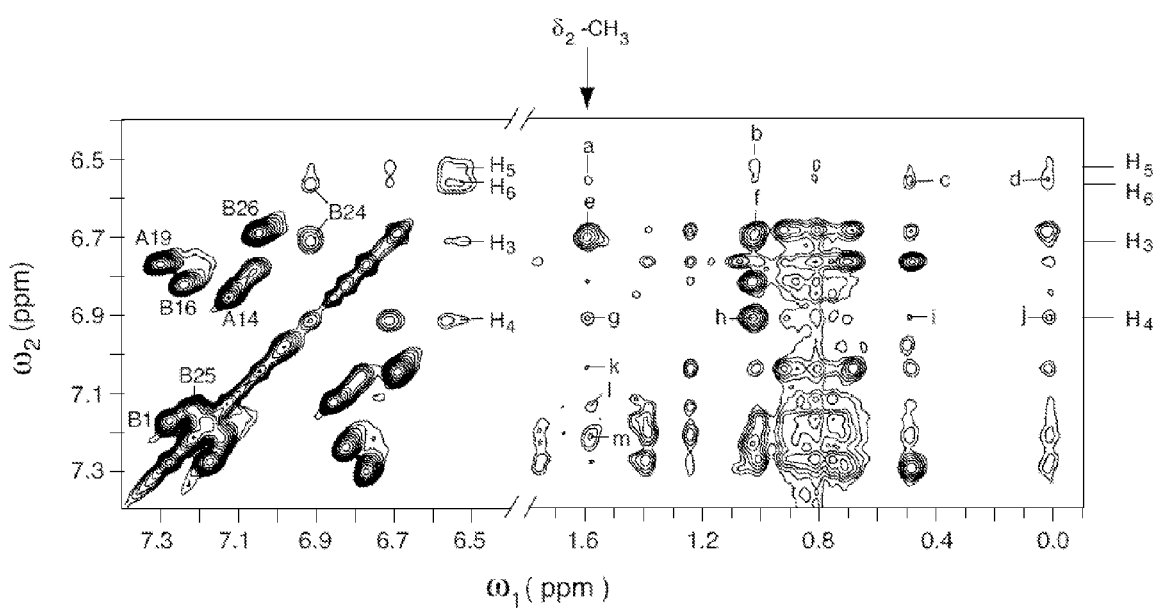
FIG. 5 provides 2D $^1$H-NMR NOESY spectra of 2-$CH_3$-$Phe^{B24}$-KP-insulin, recorded at 700 MHz at 32° C. and pD 7.0. (Left) TOCSY spectrum of aromatic region. Resonance assignments are as indicated. (Right) NOESY spectrum providing inter-proton contacts between aromatic protons (vertical axis) and aliphatic protons (horizontal axis).
Figure 6:
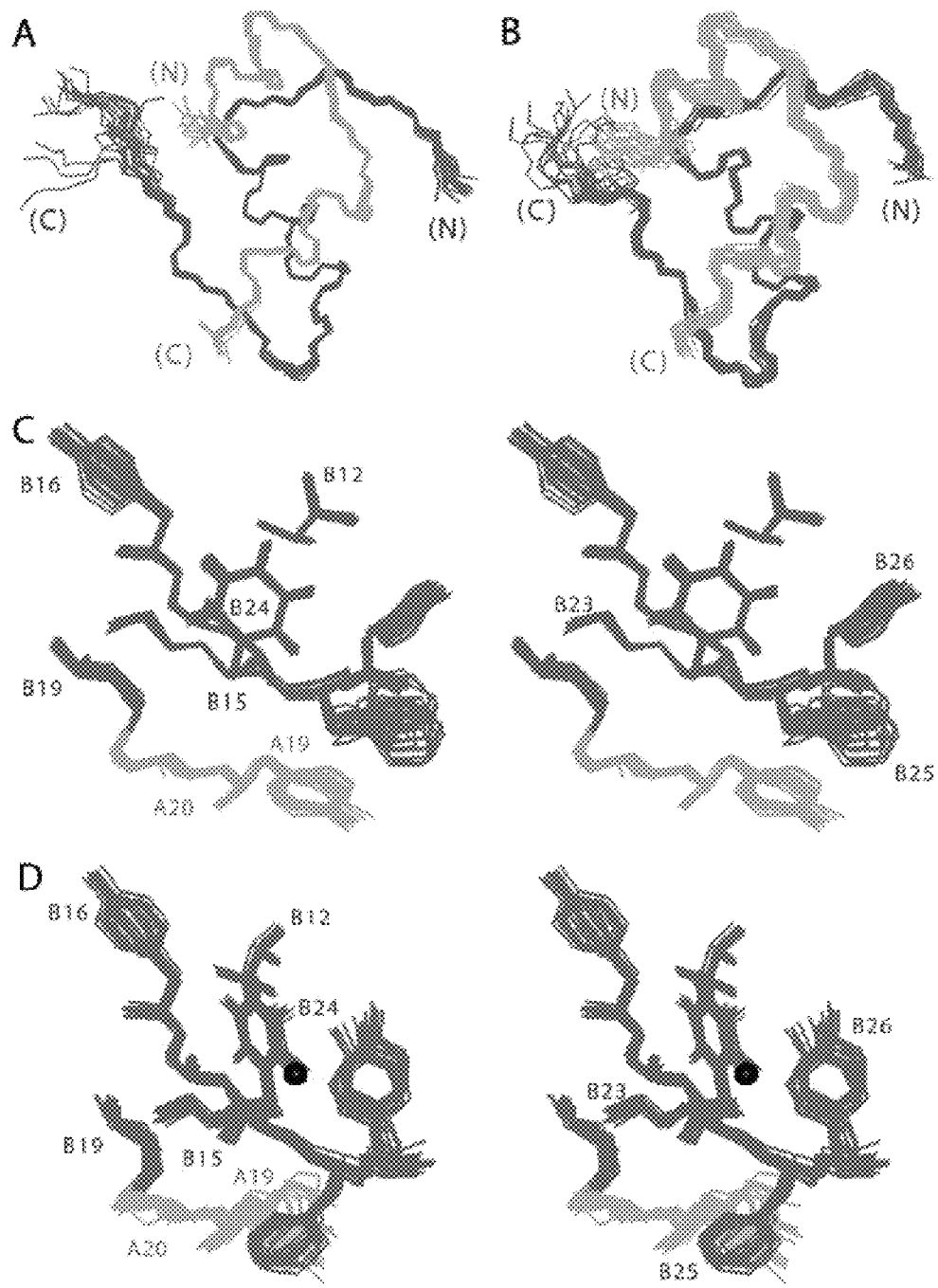
FIG. 6 depicts the solution structure of 2-$CH_3$-$Phe^{B24}$-KP-insulin as determined by 2D-NMR studies. (A) Solution structure of parent KP-insulin. The A- and B chains are shown in light and dark gray. (B) Solution structure of analogue 2-$CH_3$-$Phe^{B24}$-KP-insulin. (C and D) Detailed views of B24 side chains and neighboring residues in (C) KP-insulin and (D) 2-$CH_3$-$Phe^{B24}$-KP-insulin. The position of the nonstandard methyl group is indicated by black balls.

NMR structures of KP-insulin and the ortho-CH$_3$-Phe$^{B24}$-KP-insulin analogue have been obtained to demonstrate that substitutions is well accommodated in insulin and does not cause transmitted conformational perturbations. $^1$H-NMR spectra are provided in FIG. 5. The NMR structure of 2-CH$_3$-Phe$^{B24}$-KP-insulin as a monomer in solution is thus similar to that of KP-insulin; as shown in FIG. 6.

A series of insulin analogues containing a two amino acid addition on the carboxy end of the B-chain polypeptide were also tested for their affinity for binding to human insulin receptor isoform A (hIR-A), human insulin receptor isoform B (hIR-B) and human type 1 insulin-like growth factor receptor (hIGF-1R) by the procedure described above. Dissociation constants ($K_d$, in units of nanomolar (nM)) were calculated and are provided in Table 2 with standard error of the mean (SEM) also provided. As shown in Table 2, the analogue designated DPEE exhibits an improved ratio of binding affinity for hIR-B to hIGF-1R and an improved ratio of hIR-A to hIR-B binding affinity relative to wild type human insulin. Additionally, the analogue XKPEE, which contains both a 2-methyl-Phe$^{B24}$ substitution and the EE extension (Glu$^{B31}$, Glu$^{B32}$) with the Lys$^{B28}$, Pro$^{B29}$ substitution of Humalog®, exhibits an affinity for hIR-A and hIR-B that is as great or greater than the affinity of wild type insulin for those receptors, rather than the decreased affinity of KP insulin. XKPEE also has reduced binding affinity for hIGF-1R (approximately one half the binding affinity of wild type insulin for hIGF-1R). Similar binding affinities are observed for the analogue DPAE (Asp$^{B28}$, Pro$^{B29}$, Glu$^{B31}$, Ala$^{B32}$). While the binding affinity of DPAE for hIR-A and hIR-B is reduced compared to wild type insulin, the binding affinities are greater than that of lispro insulin (Lys$^{B28}$, Pro$^{B29}$).

The analogue denoted XDPEE (containing a 2-methyl-Phe$^{B24}$ substitution, the EE extension (Glu$^{B31}$, Glu$^{B32}$) with Asp$^{B28}$ and Pro$^{B29}$) also displays an affinity for hIR-A and hIR-B that is approximately equal to that of wild type insulin but with even less affinity for hIGF-1R than analogue XKPEE. Although the KPEE (Lys$^{B28}$, Pro$^{B29}$, Glu$^{B31}$, Glu$^{B32}$) and DPEE (Asp$^{B28}$, Pro$^{B29}$, Glu$^{B31}$, Glu$^{B32}$) analogues have reduced binding affinity for hIR-A and hIR-B, the activity of these analogues may still be sufficient to be pharmaceutically acceptable, particularly in light of their greatly reduced binding affinity for hIGF-1R. The same can also be said regarding analogues DPAE and DPDD.

TABLE 2

Binding of Insulin Analogues to Insulin Receptors and IGF-1R

| | hIR-A | | hIR-B | | hIGF-1R | |
|---|---|---|---|---|---|---|
| Analogue | $K_d$ | SEM | $K_d$ | SEM | $K_d$ | SEM |
| insulin | 0.045 | 0.007 | 0.053 | 0.008 | 6.35 | 0.96 |
| KP | 0.069 | 0.011 | 0.072 | 0.011 | 8.24 | 1.25 |
| DP | 0.060 | 0.009 | 0.064 | 0.009 | 8.64 | 1.44 |
| XKPEE | 0.043 | 0.007 | 0.040 | 0.006 | 12.80 | 2.0 |
| KPEE | 0.124 | 0.018 | 0.113 | 0.016 | 33.6 | 5.4 |
| XDPEE | 0.040 | 0.006 | 0.048 | 0.007 | 23.99 | 3.71 |

TABLE 2-continued

Binding of Insulin Analogues to Insulin Receptors and IGF-1R

| | hIR-A | | hIR-B | | hIGF-1R | |
|---|---|---|---|---|---|---|
| Analogue | $K_d$ | SEM | $K_d$ | SEM | $K_d$ | SEM |
| DPEE | 0.099 | 0.014 | 0.087 | 0.012 | 42.17 | 7.73 |
| DPEA | 0.061 | 0.009 | 0.065 | 0.010 | 20.86 | 3.62 |
| DPAE | 0.052 | 0.008 | 0.054 | 0.008 | 12.14 | 2.11 |
| DPDD | 0.084 | 0.011 | 0.115 | 0.015 | 35.12 | 5.7 |

Legend:
KP indicates insulin lispro ($Lys^{B28}$, $Pro^{B29}$);
DP indicates insulin analogue with $Asp^{B28}$ and $Pro^{B29}$;
XKPEE indicates analogue with 2-methyl-$Phe^{B24}$ (called X), $Lys^{B28}$, $Pro^{B29}$, and EE-extension ($Glu^{B31}$, $Glu^{B32}$);
KPEE indicates analogue $Lys^{B28}$, $Pro^{B29}$ with EE-extension ($Glu^{B31}$, $Glu^{B32}$);
XDPEE indicates analogue with 2-methyl-$Phe^{B24}$ (called X), $Asp^{B28}$, $Pro^{B29}$, and EE-extension ($Glu^{B31}$, $Glu^{B32}$);
DPEE indicates analogue $Asp^{B28}$, $Pro^{B29}$ with EE-extension ($Glu^{B31}$, $Glu^{B32}$);
DPEA indicates analogue $Asp^{B28}$, $Pro^{B29}$ with EA-extension ($Glu^{B31}$, $Ala^{B32}$);
DPAE indicates analogue $Asp^{B28}$, $Pro^{B29}$ with AE-extension ($Ala^{B31}$, $Glu^{B32}$);
DPDD indicates analogue $Asp^{B28}$, $Pro^{B29}$ with DD-extension ($Asp^{B31}$, $Asp^{B32}$).

A method for treating a patient comprises administering a insulin analogue containing a methyl-substituted Phe or an addition of two amino acids on the carboxyl end of the B-chain, to the patient. In one example, the methyl-substituted insulin analogue is an insulin analogue containing methyl-substituted phenylalanine at position B24. In one particular example the methyl-substituted phenylalanine is 2-$CH_3$-$Phe^{B24}$, 3-$CH_3$-$Phe^{B24}$, or 4-$CH_3$-$Phe^{B24}$. In another example, the insulin analogue includes an addition of two amino acids on the carboxy terminal end of the insulin B-chain selected from a glutamate addition ($Glu^{B31}$) or an aspartate addition ($Asp^{B31}$) and an additional addition selected from glutamate ($Glu^{B32}$), alanine ($Ala^{B32}$) and aspartate ($Asp^{B32}$). In one particular example, the addition to the carboxy-terminal end of the insulin B-chain is $Glu^{B31}$, $Glu^{B32}$. In a further example, the insulin analogue contains both a methyl-substituted phenylalanine at position B24 and an addition of two amino acids on the carboxy terminal end of the insulin B-chain as described above.

In still another example, the insulin analogue is administered by an external or implantable insulin pump. An insulin analogue of the present invention may also contain other modifications, such as a tether between the C-terminus of the B-chain and the N-terminus of the A-chain as described more fully in co-pending U.S. patent application Ser. No. 12/419,169, the disclosure of which is incorporated by reference herein.

A pharmaceutical composition may comprise such insulin analogues and which may optionally include zinc. Zinc ions may be included in such a composition at a level of a molar ratio of between 2.2 and 3.0 per hexamer of the insulin analogue. In such a formulation, the concentration of the insulin analogue would typically be between about 0.1 and about 3 mM; concentrations up to 3 mM may be used in the reservoir of an insulin pump. Modifications of meal-time insulin analogues may be formulated as described for (a) "regular" formulations of Humulin™ (Eli Lilly and Co.), Humalog™ (Eli Lilly and Co.), Novalin™ (Novo-Nordisk), and Novalog™ (Novo-Nordisk) and other rapid-acting insulin formulations currently approved for human use, (b) "NPH" formulations of the above and other insulin analogues, and (c) mixtures of such formulations.

Excipients may include glycerol, glycine, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

A nucleic acid comprising a sequence that encodes a polypeptide encoding an insulin analogue containing a sequence encoding at least a B-chain of insulin with a methylated phenylalanine at position B24 is also envisioned. This can be accomplished through the introduction of a stop codon (such as the amber codon, TAG) at position B24 in conjunction with a suppressor tRNA (an amber suppressor when an amber codon is used) and a corresponding tRNA synthetase, which incorporates a non-standard amino acid into a polypeptide in response to the stop codon, as previously described (Furter, 1998, *Protein Sci.* 7:419-426; Xie et al., 2005, *Methods.* 36: 227-238). The particular sequence may depend on the preferred codon usage of a species in which the nucleic acid sequence will be introduced. The nucleic acid may also encode other modifications of wild-type insulin. The nucleic acid sequence may encode a modified A- or B-chain sequence containing an unrelated substitution or extension elsewhere in the polypeptide or modified proinsulin analogues. The nucleic acid may also be a portion of an expression vector, and that vector may be inserted into a host cell such as a prokaryotic host cell like an *E. coli* cell line, or a eukaryotic cell line such as *S. cereviciae* or *Pischia pastoris* strain or cell line.

For example, it is envisioned that synthetic genes may be synthesized to direct the expression of a B-chain polypeptide in yeast *Piscia pastoris* and other microorganisms. The nucleotide sequence of a B-chain polypeptide utilizing a stop codon at position B24 for the purpose of incorporating a methylated phenylalanine at that position may be either of the following or variants thereof:

(a) with Human Codon Preferences:
(SEQ. ID. NO. 22)
TTTGTGAACCAACACCTGTGCGGCTCACACCTGGTGGAAGCTCTCTACCT

AGTGTGCGGGAACGAGGCTAGTTCTACACACCCAAGACC (b) with Pichia Codon Preferences:
(SEQ. ID. NO. 23)
TTTGTTAACCAACATTTGTGTGGTTCTCATTTGGTTGAAGCTTTGTACTT

GGTTTGTGGTGAAAGAGGTTAGTTTTACACTCCAAAGACT

Similarly, a full length pro-insulin cDNA having human codon preferences and utilizing a stop codon at position B24 for the purpose of incorporating a methylated phenylalanine at that position may have the sequence of SEQ. ID NO. 24.

(SEQ.ID. NO. 24)
TTTGTGAACC AACACCTGTG CGGCTCACAC CTGGTGGAAG

CTCTCTACCT AGTGTGCGGG GAACGAGGCT AGTTCTACAC

ACCCAAGACC CGCCGGGAGG CAGAGGACCT GCAGGTGGGG

CAGGTGGAGC TGGGCGGCGG CCCTGGTGCA GGCAGCCTGC

AGCCCTTGGC CCTGGAGGGG TCCCTGCAGA AGCGTGGCAT

TGTGGAACAA TGCTGTACCA GCATCTGCTC CCTCTACCAG

CTGGAGAACT ACTGCAACTA G

Likewise, a full length human pro-insulin cDNA utilizing a stop codon at position B24 for the purpose of incorporating a methylated phenylalanine at that position and having codons preferred by *P. pastoris* may have the sequence of SEQ. ID. NO. 25.

(SEQ. ID. NO. 25)

```
TTTGTTAACC AACATTTGTG TGGTTCTCAT TTGGTTGAAG

CTTTGTACTT GGTTTGTGGT GAAAGAGGTT AGTTTTACAC

TCCAAAGACT AGAAGAGAAG CTGAAGATTT GCAAGTTGGT

CAAGTTGAAT TGGGTGGTGG TCCAGGTGCT GGTTCTTTGC

AACCATTGGC TTTGGAAGGT TCTTTGCAAA AGAGAGGTAT

TGTTGAACAA TGTTGTACTT CTATTTGTTC TTTGTACCAA

TTGGAAAACT ACTGTAACTA A
```

Other variants of these sequences, encoding the same polypeptide sequence, are possible, given the synonyms in the genetic code.

Based upon the foregoing disclosure, it should now be apparent that insulin analogues provided will carry out the objects set forth hereinabove. Namely, these insulin analogues exhibit enhanced thermodynamic stability, resistance to fibrillation and potency in reducing blood glucose levels. The methyl substituted phenylalanine-containing insulin analogues also have reduced cross-reactivity to insulin-like growth factor (IGFR). It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Furter, R., 1998. Expansion of the genetic code: Site-directed p-fluoro-phenylalanine incorporation in *Escherichia coli*. *Protein Sci.* 7:419-426.

Merrifield, R. B., Vizioli, L. D., and Boman, H. G. 1982. Synthesis of the antibacterial peptide cecropin A (1-33). *Biochemistry* 21: 5020-5031.

Mirmira, R. G., and Tager, H. S. 1989. Role of the phenylalanine B24 side chain in directing insulin interaction with its receptor: Importance of main chain conformation. *J. Biol. Chem.* 264: 6349-6354.

Sosnick, T. R., Fang, X., and Shelton, V. M. 2000. Application of circular dichroism to study RNA folding transitions. *Methods Enzymol.* 317: 393-409.

Wang, Z. X. 1995. An exact mathematical expression for describing competitive biding of two different ligands to a protein molecule *FEBS Lett.* 360: 111-114.

Weiss, M. A., Hua, Q. X., Jia, W., Chu, Y. C., Wang, R. Y., and Katsoyannis, P. G. 2000. Hierarchiacal protein "un-design": insulin's intrachain disulfide bridge tethers a recognition α-helix. *Biochemistry* 39: 15429-15440.

Whittaker, J., and Whittaker, L. 2005. Characterization of the functional insulin binding epitopes of the full length insulin receptor. *J. Biol. Chem.* 280: 20932-20936.

Xie, J. and Schultz, P. G. 2005. An expanding genetic code. *Methods.* 36: 227-238.

What is claimed is:

1. An insulin analogue comprising an insulin B-chain polypeptide containing at least one alteration selected from:
   a methylated phenylalanine substitution at position B24; and
   an addition of two amino acids to the carboxyl end of the B-chain polypeptide, wherein a first amino acid at position B31 is selected from glutamate and aspartate, and a second amino acid at position B32 is selected from glutamate, alanine and aspartate.

2. The insulin analogue of claim 1, wherein the methylated phenylalanine is ortho-monomethyl-phenylalanine, meta-monomethyl-phenylalanine or para-monomethyl-phenylalanine.

3. The insulin analogue of claim 2, wherein the methylated phenylalanine is ortho-monomethyl-phenylalanine.

4. The insulin analogue of claim 1, wherein at least one of the first and second amino acids is glutamate.

5. The insulin analogue of claim 4, wherein the first amino acid and the second amino acid are both glutamate.

6. The insulin analogue of claim 1, wherein the insulin B-chain polypeptide comprises both a methylated phenylalanine substitution at position B24 and an addition of two amino acids to the carboxyl end of the B-chain polypeptide, wherein a first amino acid at position B31 is selected from glutamate and aspartate, and a second amino acid at position B32 is selected from glutamate, alanine and aspartate.

7. The insulin analogue of claim 6, wherein the methylated phenylalanine is ortho-monomethyl-phenylalanine.

8. The insulin analogue of claim 7, wherein at least one of the first and second amino acids is glutamate.

9. The insulin analogue of claim 8, wherein the first amino acid and the second amino acid are both glutamate.

10. The insulin analogue of claim 9, additionally comprising a paired substitution selected from a lysine substitution at position B28 with a proline substitution at position B29, or an aspartate substitution at position B28 with a proline substitution at position B29.

11. The insulin analogue of claim 8, additionally comprising a paired substitution selected from a lysine substitution at position B28 with a proline substitution at position B29, or an aspartate substitution at position B28 with a proline substitution at position B29.

12. The insulin analogue of claim 1, wherein the analogue is an analogue of a mammalian insulin.

13. The insulin analogue of claim 12, wherein the analogue is an analogue of human insulin.

14. The insulin analogue of claim 13, wherein the B-chain polypeptide comprises an amino acid sequence of SEQ. ID. NO. 26.

15. A method of treating diabetes in a patient in need thereof comprising administering a physiologically effective amount of an insulin analogue or a physiologically acceptable salt thereof to the patient, wherein the insulin analogue or a physiologically acceptable salt thereof contains a B-chain polypeptide incorporating at least one alteration selected from:
   a methylated phenylalanine at position B24, and
   an addition of two amino acids to the carboxyl end of the B-chain polypeptide, wherein a first amino acid at position B31 is selected from glutamate and aspartate, and a second amino acid at position B32 is selected from glutamate, alanine and aspartate.

* * * * *